United States Patent
Joye et al.

[11] Patent Number: 5,971,979
[45] Date of Patent: Oct. 26, 1999

[54] METHOD FOR CRYOGENIC INHIBITION OF HYPERPLASIA

[75] Inventors: James Joye, Sewicky, Pa.; Ronald Williams, Menlo Park, Calif.

[73] Assignee: Odyssey Technologies, Inc., Menlo Park, Calif.

[21] Appl. No.: 08/982,824

[22] Filed: Dec. 2, 1997

[51] Int. Cl.⁶ ............................................. A61B 17/36
[52] U.S. Cl. ........................................... 606/21; 128/898
[58] Field of Search .................. 606/20, 21, 22, 606/23, 26, 192, 194; 128/DIG. 27, 898; 607/104; 604/96, 101, 104

[56] References Cited

U.S. PATENT DOCUMENTS

| | | |
|---|---|---|
| 3,901,241 | 8/1975 | Allen, Jr. . |
| 4,336,691 | 6/1982 | Burstein et al. ............................ 62/64 |
| 4,754,752 | 7/1988 | Ginsburg et al. . |
| 5,019,075 | 5/1991 | Spears et al. ............................... 606/7 |
| 5,041,089 | 8/1991 | Mueller et al. ............................ 604/96 |
| 5,078,713 | 1/1992 | Varney ...................................... 606/23 |
| 5,092,841 | 3/1992 | Spears ....................................... 604/96 |
| 5,106,360 | 4/1992 | Ishiwara et al. ............................ 600/2 |
| 5,147,355 | 9/1992 | Friedman et al. ......................... 606/23 |
| 5,151,100 | 9/1992 | Abele et al. ............................... 606/28 |
| 5,190,539 | 3/1993 | Fletcher et al. ............................ 606/25 |
| 5,191,883 | 3/1993 | Lennox et al. . |
| 5,196,024 | 3/1993 | Barath ...................................... 606/191 |
| 5,275,595 | 1/1994 | Dobak, III ................................. 606/23 |
| 5,458,612 | 10/1995 | Chin ........................................ 606/192 |
| 5,486,208 | 1/1996 | Ginsburg .................................. 607/106 |
| 5,501,681 | 3/1996 | Neuwirth et al. .......................... 606/21 |
| 5,545,195 | 8/1996 | Lennox et al. ............................ 607/105 |
| 5,617,739 | 4/1997 | Little ....................................... 62/619 |
| 5,644,502 | 7/1997 | Little ...................................... 364/496 |
| 5,733,280 | 3/1998 | Avitall ..................................... 606/23 |
| 5,868,735 | 2/1999 | Lafontaine ................................ 606/21 |

FOREIGN PATENT DOCUMENTS

| | | | |
|---|---|---|---|
| WO 91/05528 | 2/1991 | WIPO . | |
| WO 98/49957 | 11/1998 | WIPO .......................... | A61B 17/39 |

OTHER PUBLICATIONS

Gage, M.D., Andrew A., et al., "Freezing injury to large blood vessels in dogs," Surgery, vol. 61, No. 5, May, 1997, pp. 748–754.

*Primary Examiner*—Linda C. M. Dvorak
*Assistant Examiner*—Rosilund Kearney
*Attorney, Agent, or Firm*—Townsend and Townsend and Crew LLP

[57] ABSTRACT

Post-angioplasty hyperplasia in blood vessels is treated using a cryosurgical balloon catheter. The balloon catheter is positioned at a target region within the blood vessel, and the balloon inflated by expanding a cryogenic fluid, such as liquid nitrogen, across an expansion orifice into a balloon. The balloon will be constructed so that cooling is achieved primarily in the central regions of the balloon, with the proximal and distal regions being less cold and acting to insulate adjacent regions of the blood vessel from excessive cooling.

20 Claims, 4 Drawing Sheets

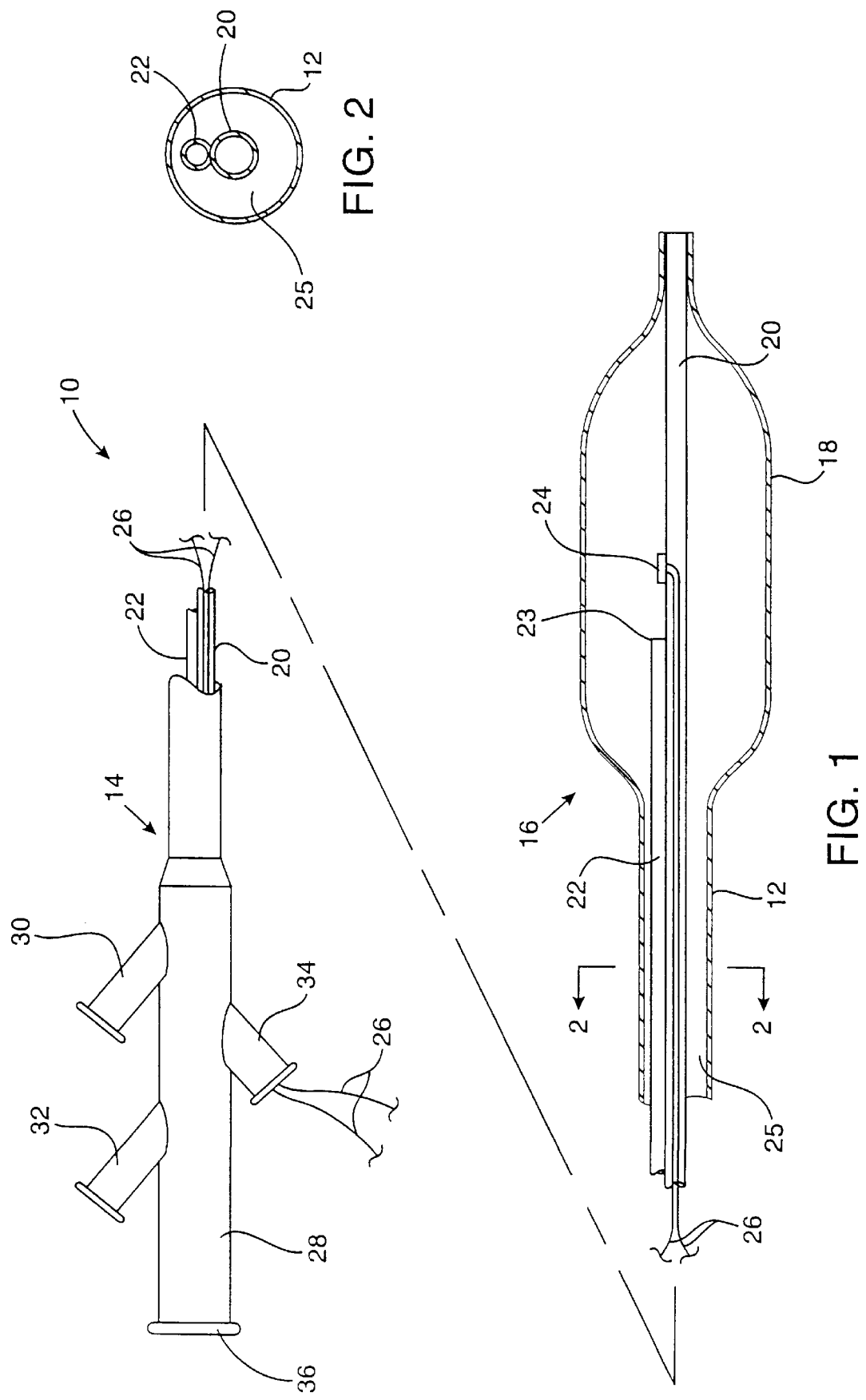

METHOD FOR CRYOGENIC INHIBITION OF HYPERPLASIA

BACKGROUND OF THE INVENTION

1. Field of the Invention

The present invention relates generally to apparatus and methods for inhibiting restenosis in arteries following angioplasty or other intravascular procedures for treating atherosclerotic disease. More particularly, the present invention relates to apparatus and methods for cryogenically treating the target site within a patient's vasculature to inhibit hyperplasia which can occur after such intravascular procedures.

A number of percutaneous intravascular procedures have been developed for treating atherosclerotic disease in a patient's vasculature. The most successful of these treatments is percutaneous transluminal angioplasty (PTA) which employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these procedures, particularly PTA, have gained wide acceptance, they continue to suffer from the subsequent occurrence of restenosis.

Restenosis refers to the re-narrowing of an artery within weeks or months following an initially successful angioplasty or other primary treatment. Restenosis afflicts up to 50% of all angioplasty patients and results at least in part from smooth muscle cell proliferation in response to the injury caused by the primary treatment, generally referred to as "hyperplasia." Blood vessels in which significant restenosis occurs will require further treatment.

A number of strategies have been proposed to treat hyperplasia and reduce restenosis. Such strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While enjoying different levels of success, no one of these procedures has proven to be entirely successful in treating all occurrences of restenosis and hyperplasia.

For these reasons, it would be desirable to provide additional apparatus and methods suitable for the treatment of restenosis and hyperplasia in blood vessels. It would be further desirable if the apparatus and methods were suitable for treatment of other conditions related to excessive cell proliferation, including neoplasms resulting from tumor growth, hyperplasia in other body lumens, and the like. The apparatus and method should be suitable for intravascular and intraluminal introduction, preferably via percutaneous access. It would be particularly desirable if the methods and apparatus were able to deliver the treatment in a very focused and specific manner with minimal effect on adjacent tissues. Such apparatus and methods should further be effective in inhibiting hyperplasia and/or neoplasia in the target tissue with minimum side affects. At least some of these objectives will be met by the invention described hereinafter.

2. Description of the Background Art

Balloon catheters for intravascularly cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691.

The full disclosures of each of the above U.S. Patents are incorporated herein by reference.

SUMMARY OF THE INVENTION

The present invention comprises the cryosurgical treatment of a target site within the body lumen of a patient, usually in an artery which has been previously treated for atherosclerotic disease by balloon angioplasty or any of the other primary treatment modalities described above. The present invention, however, is further suitable for treating other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Inhibition of such excessive cell growth is necessary to maintain patency of the lumen.

Treatment according to the present invention is effected by cooling target tissue to a temperature which is sufficiently low for a time which is sufficiently long to inhibit excessive cell proliferation. The cooling treatment will be directed against all or a portion of a circumferential surface of the body lumen, and will preferably result in cell growth inhibition, but not necessarily in significant cell necrosis. Particularly in the treatment of arteries following balloon angioplasty, cell necrosis may be undesirable if it increases the hyperplastic response. Thus, the present invention will slow or stop cell proliferation but may leave the cells which line the body lumen viable, thus lessening hyperplasia.

Methods according to the present invention comprise cooling an inner surface of the body lumen to a temperature and for a time sufficient to inhibit subsequent cell growth. Usually, the temperature at the cell surface is in the range from $-20°$ C. to $-80°$ C., preferably from $-30°$ C. to $-50°$ C. The tissue is maintained at the described temperature for a time period in the range from 1 second to 10 seconds, preferably from 2 seconds to 5 seconds. In the case of arteries, the cooling treatment will usually be effected very shortly after angioplasty or other primary treatment procedure, preferably within one hour of the primary treatment, more preferably within thirty minutes within the primary treatment, and most preferably immediately following the primary treatment.

The methods of the present invention may be performed with cryosurgical catheters comprising a catheter body having a proximal end, a distal end, and a primary lumen therethrough. The primary lumen terminates in a Joule-Thomson orifice at or near its distal end, and a balloon is disposed over the orifice on the catheter body to contain a cryogenic fluid delivered through the primary lumen. Suitable cryogenic fluids will be non-toxic and include liquid nitrogen, liquid nitrous oxide, and the like. By delivering the cryogenic fluid through the catheter body, the balloon can be expanded and cooled in order to effect treatments according to the present invention.

Preferably, the Joule-Thomson orifice will be spaced inwardly from each end of the balloon and the balloon will be sufficiently long so that the cooling of the balloon occurs primarily in the middle. The temperature of the proximal and distal ends of the balloon will thus be much less than that of the middle, and the ends will thus act as "insulating" regions which protect luminal surfaces and other body structures from unintended cooling. Preferably, the balloon has a length of at least 1 cm, more preferably at least 2 cm, and typically in the range from 3 cm to 10 cm. The orifice is usually positioned at least 0.5 cm from each end, preferably being at least 1 cm from each end in balloons which are 2 cm or longer.

While it has been found that positioning of the Joule-Thomson valve in the central region of a balloon will usually provide sufficient insulation of each end resulting from the inherent heat transfer characteristics, in some instances it will be desirable to provide a separate containment bladder nested inside the balloon to receive the cryogenic fluid. The containment bladder will further act to limit cooling to the central region of the balloon. The portions of the balloon proximal and distal to the containment bladder may optionally be inflated with an insulating medium, such as a gas, silicone oil, saline, or the like. Alternatively, the containment bladder may have a vent or be partially porous so that the cryogenic fluid (which is present as a gas within the containment bladder) flows at a controlled rate into the overlying balloon. By limiting the flow rate, the temperature of the cryogenic fluid will be significantly higher in the regions outside of the containment bladder but still within the balloon.

BRIEF DESCRIPTION OF THE DRAWINGS

FIG. 1 illustrates a cryosurgical catheter constructed in accordance with the principles of the present invention, with a distal end shown in cross-section.

FIG. 2 is a cross-sectional view of the catheter taken along line 2—2 in FIG. 1.

DESCRIPTION OF THE SPECIFIC EMBODIMENTS

Figure 4:
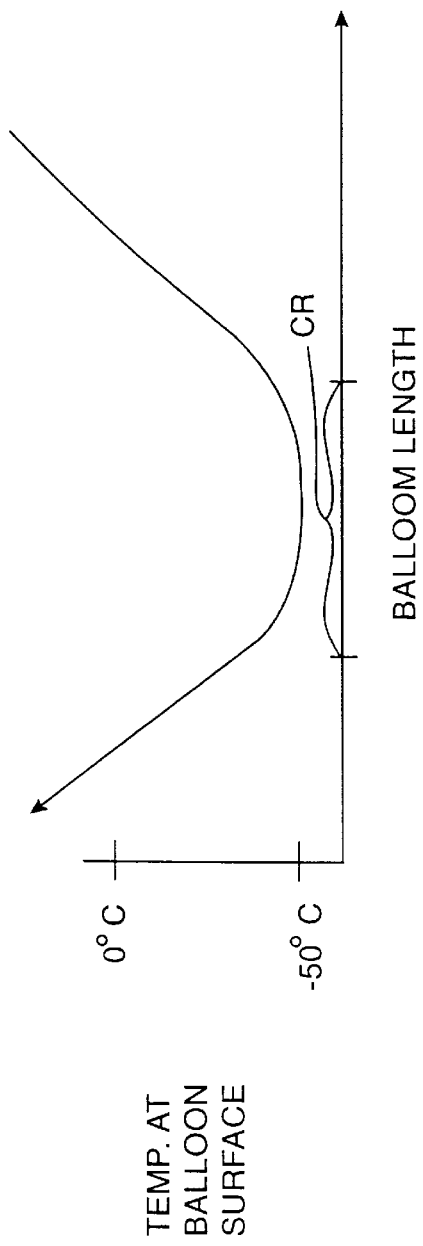
FIG. 4 is a graph illustrating the temperature profile of the balloon of FIGS. 1 and 3 while liquid nitrogen is being expanded therein and the balloon is present in a body lumen.

An exemplary cryosurgical catheter 10 constructed in accordance with the principles of the present invention is illustrated in FIGS. 1 and 2. The catheter 10 comprises a catheter body 12 having a proximal end 14, a distal end 16, and an inflatable balloon 18 disposed at the distal end. The balloon 18 is shown to be an integral extension of the catheter body 12, but such a structure is not required by the present invention. The balloon could be formed from the same or a different material and, in the latter case, attached to the distal end of the catheter body 12 by suitable adhesives, heat welding, or the like. The catheter body may be formed from conventional materials, such as polyethylenes, polyimides, and copolymers and derivatives thereof. The balloon may also be formed from conventional materials used for angioplasty balloons, typically being non-distensible, such as polyethylene.

Catheter 10 comprises a central shaft 20 which may be formed from polymeric material, such as polyethylene, polytetrafluoroethylene, polyimide, or from a metal, such as from hypotube. In the embodiment of catheter 10, the coaxial shaft 20 is tubular and provides a guidewire lumen for positioning of the catheter over a guidewire in a conventional manner. The shaft 20, however, could have a variety of other configurations and purposes. For example, the shaft could be a solid wire or core and further optionally provide a guidewire tip at its distal end. The shaft could also provide a lumen for delivering cryogenic fluid to the balloon 18. In the illustrated embodiment of FIG. 10, however, the cryogenic fluid is provided by a separate cryogenic fluid delivery tube 22 which is disposed in parallel to the coaxial shaft 20.

The catheter 10 will usually further comprise a thermocouple 24 which is optimally located near the center of balloon 18. At this location, it can measure the temperature of the cryogenic fluid after expansion from the proximal end of the cryogenic delivery tube 22. The cryogenic delivery tube 22 will define an expansion orifice at its distal end 23. Thus, the cryogenic fluid will flow through the tube 22 as a liquid at an elevated pressure and (thus inhibiting flow restrictive film boiling) will expand across the orifice 23 to a gaseous state at a lower pressure within the balloon. For liquid nitrogen, the pressure within the tube 22 will typically be in the range from 50 psi to 500 psi at a temperature below the associated boiling point. After expansion, the nitrogen gas within the balloon near its center (the location of thermocouple 24) the pressure will typically be in the range form 30 psi to 100 psi and the temperature in the range from −40° C. to −100° C. The temperature, of course, will decrease in both the radially outward direction and in both axial directions from the center of the balloon. This feature of the present invention is better described in connection with FIGS. 3 and 4 below.

A hub 28 is secured to the proximal end 14 of the catheter body 12. The hub provides for a port 30 for connecting a cryogenic fluid source to the cryogenic delivery tube 22. The hub further provides a port 32 for exhausting the gaseous cryogenic fluid which travels from balloon 18 in a proximal direction through annular lumen 25. A third port 34 is provided for thermocouple wires 26. A fourth port 36 at the proximal end of the hub is provided for a guidewire.

Figure 3:
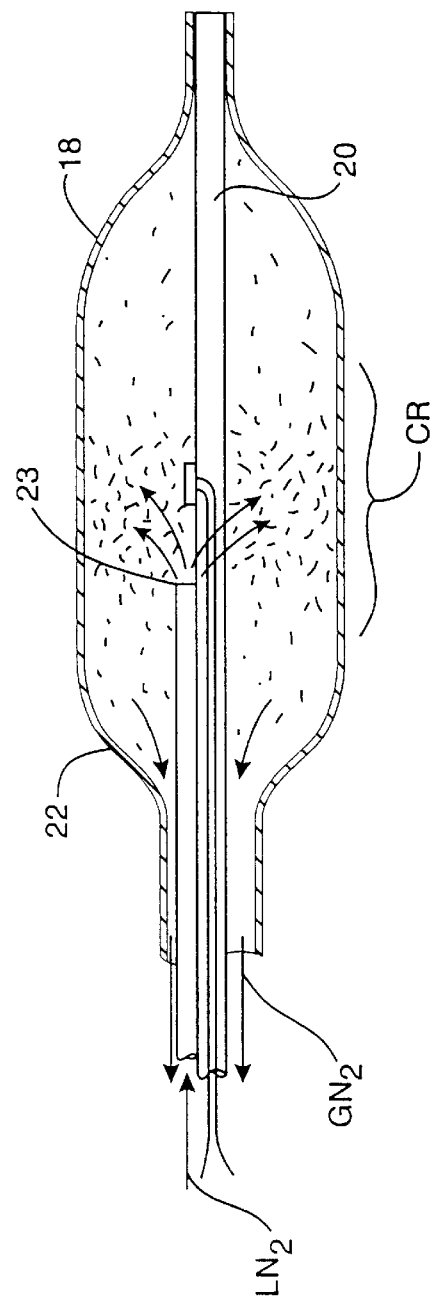
FIG. 3 illustrates the expansion of a cryogenic fluid within the balloon of the cryosurgical catheter of FIG. 1.

Referring now to FIGS. 3 and 4, liquid nitrogen ($LN_2$) is delivered to balloon 18 through the cryogenic delivery tube 22. The liquid nitrogen is delivered at a temperature and pressure within in the ranges set forth above and expands to gaseous nitrogen ($GN_2$) across the expansion orifice into the interior of balloon 18. In the single-balloon embodiment catheter 10, the gaseous nitrogen will serve both to inflate the balloon 18 and to cool the exterior surface of the balloon in a desired temperature profile. In particular, the balloon dimensions and operating conditions will be selected to provide a particular balloon temperature profile, an example of which is set forth in FIG. 4. By expanding the liquid nitrogen to its gaseous state near the center of the balloon, the balloon temperature will be lowest near the center and will decrease in both axial directions away from the center, as shown in the temperature profile of FIG. 4. For treating arterial hyperplasia, it is presently believed that a balloon temperature in the range from −20° C. to −80° C., e.g., at about −50° C., for a time period in the range from 1 second to 10 seconds, will be effective. By delivering the liquid nitrogen at a pressure in the range from 50 psi to 500 psi and at a temperature below the boiling point, and expanding the liquid nitrogen to a gas at a pressure in the range from 30 psi to 100 psi, a temperature in the desired range at the middle of the balloon will be achieved. Moreover, by extending the balloon by distances of at least 0.5 cm, preferably of at least 1 cm, in each direction from the center of the balloon, the temperatures at the ends of the balloons will generally no lower than 0° C. In this way, a desired low temperature can be maintained at the outer surface of the balloon in a treatment region near the center of the balloon, while the distal and proximal ends of the balloon act to insulate the colder portions from non-target regions within the artery or other body lumen. It will be appreciated that the axial length of the treatment region of the balloon can be varied considerably by varying the length of the balloon and controlling the volume of liquid nitrogen delivered to the balloon. Exemplary balloons will have a length in the range from 3 cm to 5 cm, a diameter in the range from 1.5 mm to 4 mm, and will typically receive from 0.08 ml/sec to 1.5 ml/sec of liquid nitrogen in the temperature and pressure ranges set forth above.

Figure 5:
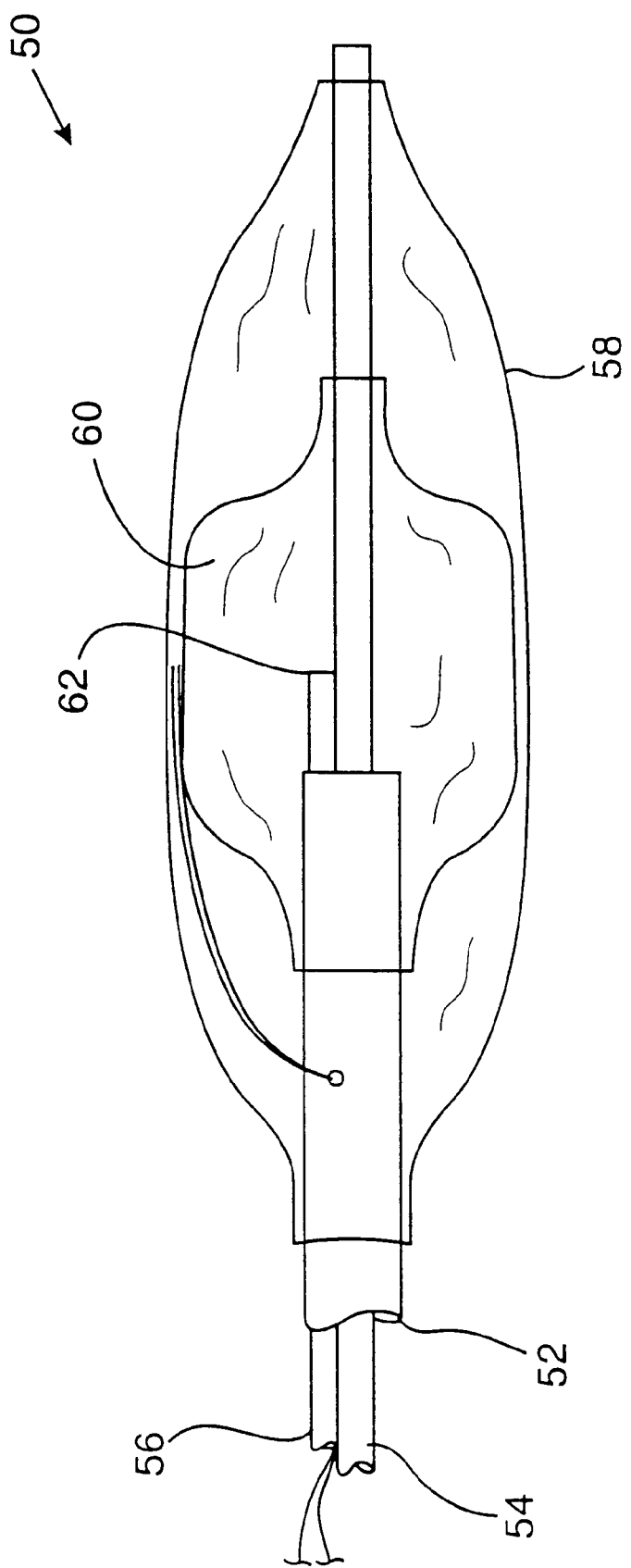
FIG. 5 illustrates the distal end of a cryosurgical catheter constructed in accordance with the principles of the present invention and having a nested containment bladder within a balloon structure.

Referring now to FIG. 5, an alternative balloon assembly 50 will be described. The balloon assembly 50 is disposed at the distal end of a catheter body 52 comprising a shaft 54 and a cryogenic fluid delivery tube 56. A balloon 58 is secured to the distal end of the catheter body 52, generally as described above with respect to catheter 10. In contrast to catheter 10, however, balloon assembly 50 comprises a containment bladder 60 nested within the balloon 58. The containment bladder 50 may be a second balloon formed in a manner similar to balloon 58, except that it will be shorter and will have proximal and distal ends spaced axially inwardly from the proximal and distal ends of balloon 58. The bladder 60, however, may be disposed of different materials and have different properties. Generally, the containment bladder is intended to receive and contain the gaseous nitrogen after it is expanded across expansion orifice 62 into the interior thereof. By containing the expanded (cold) gaseous nitrogen within bladder 60, a more distinct temperature transition may be effected between the cold middle region of balloon 58 and the less cold distal and proximal regions thereof.

Optionally, the balloon 58 may be separately expanded with an insulating fluid to further sharpen the temperature transition between the containment bladder 60 and the remainder of balloon 58. Alternatively, the containment bladder 60 may include ports or porous regions which permit the gaseous nitrogen to pass from the interior of the bladder 60 into the interior of balloon 58 in a controlled manner to maintain the desired temperature transition.

Figure 6A:
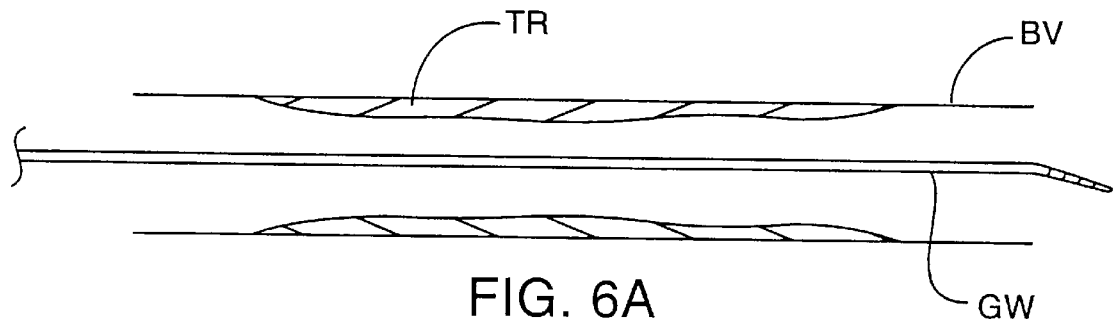
FIG. 6A–6C illustrate use of the catheter of FIG. 1 in treating a target site within a patient's vasculature.
Figure 6B:
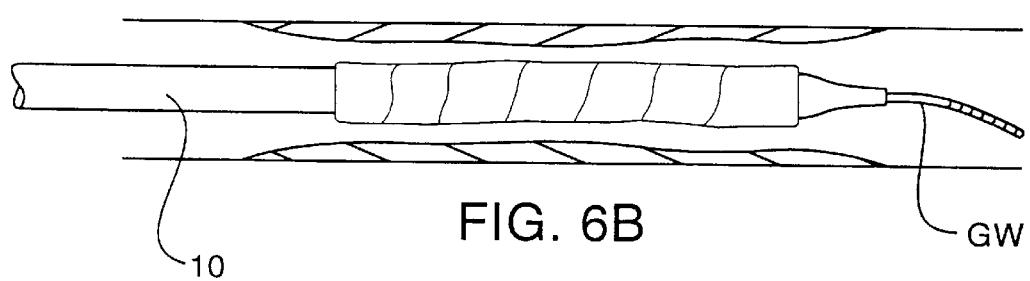
Figure 6C:
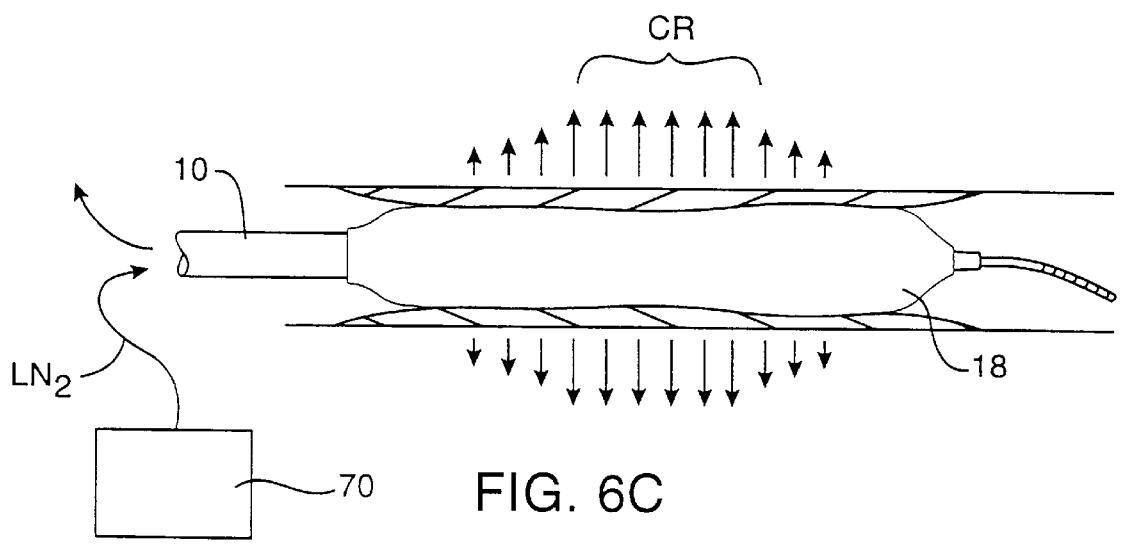

Referring now to FIGS. 6A–6C, use of catheter 10 for treating a target region TR within a blood vessel BV will be described. The target region will usually have been previously treated by balloon angioplasty or other primary conventional protocol for treating atherosclerotic disease. Such primary treatment will typically utilize an intravascular catheter, which catheter will have been removed leaving a guidewire GW in place, as illustrated in FIG. 6A. A catheter 10 is then introduced over the guidewire, as illustrated in FIG. 6B. Liquid nitrogen is introduced to the catheter 10 from a suitable source 70. The source may be a Dewar flask or other conventional source. In some instances, it will be possible to utilize recirculating refrigerated liquid nitrogen sources, such as those described in U.S. Pat. Nos. 5,644,502 and 5,617,739, the full disclosures of which have been previously incorporated herein by reference. The liquid nitrogen ($LN_2$) is delivered to the catheter 10 and inflates balloon 18, as illustrated in FIG. 6C. Because of the temperature profile of the balloon, cooling of the inner wall of the blood vessel BV will be maximized over a central region CR and diminish in the proximal and distal directions from the central region, as illustrated qualitatively by the array of arrows in FIG. 6C. The treatment will be performed at the temperatures and for the times described thereabove in order to inhibit subsequent hyperplasia of the cells of the lining of the blood vessel. Advantageously, the cryogenic methods of the present invention will inhibit subsequent cell proliferation without inducing injury and thrombosis which can occur as a result of such injury.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating hyperplasia or neoplasia in a body lumen, said method comprising:

cooling an inner surface of the body lumen to a temperature and for a time sufficient to inhibit subsequent cell growth, the cooling step comprising:
introducing a catheter into the body lumen;
positioning a central region of a balloon on the catheter proximate a target site within the body lumen, the central region disposed between first and second ends of the balloon; and
expanding a gas within the balloon to cryogenically cool the target site through the central region; and
inhibiting cooling through the proximal and distal ends of the balloon relative to the central region during the cooling step.

2. A method as in claim 1, wherein the body lumen is an artery subject to hyperplasia resulting from treatment of a stenosis.

3. A method as in claim 2, wherein the treatment of the stenosis comprises balloon angioplasty.

4. A method as in claim 2, wherein the cooling step is performed within one hour following treatment of the stenosis.

5. A method as in claim 1, wherein the cooling step comprises lowering the temperature of the lumenal surface to from −20° C. to −80° C. for a time period in the range from 1 second to 10 seconds.

6. A method as in claim 1, wherein the expanding step comprises flowing liquid nitrogen to a Joule-Thomson orifice positioned within the balloon so that the nitrogen expands across the orifice.

7. A method as in claim 6, wherein the pressure within the balloon is maintained at from 30 psi to 100 psi and the temperature near the orifice is in the range from −40° C. to −100° C.

8. A method as in claim 1, wherein the inhibiting step is performed so that a temperature at each end of the balloon is above 0° C.

9. A method as in claim 1, wherein the balloon has a length of at least 1 cm and the inhibiting step comprises positioning a gas expansion orifice at least 0.5 cm from each end.

10. A method as in claim 1, wherein the gas expanding and inhibiting steps are performed so as to produce a temperature profile over the length of the balloon with a temperature between the ends below −20° C. and temperatures at each end above 0° C.

11. A method as claimed in claim 1, wherein the balloon is elongate, and wherein the gas expanding and inhibiting steps are performed so that more cooling is provided through the central region than through the ends of the balloon.

12. A method as claimed in claim 1, wherein the balloon is elongate, and wherein the gas expanding and inhibiting steps are performed so that the central region is at a lower temperature than the ends of the balloon.

13. A method as claimed in claim 1, wherein the inhibiting step comprises separating the gas from the ends of the balloon with a containment bladder, the containment bladder engaging the central region of the balloon.

14. A method as claimed in claim 13 wherein the gas expanding step inflates the containment bladder.

15. A method for treating hyperplasia of a blood vessel, the blood vessel having a target site along an inner surface, the target site subject to hyperplasia resulting from treatment of a stenosis, said method comprising:

introducing a catheter into the blood vessel;

positioning a balloon on the catheter proximate the target site within the blood vessel; and inflating the balloon by expanding a gas within the balloon so that gas urges the balloon radially outwardly against the target site of the blood vessel, and so that the expanding gas cools an inner surface of the blood vessel to a temperature and for a time sufficient to inhibit subsequent excessive cell proliferation.

16. A method as claimed in claim 15, further comprising insulating the expanding gas from proximal and distal ends of the balloon so that cooling through a central region of the balloon is greater than cooling through the proximal end distal ends of the balloon.

17. A method as claimed in claim 16, wherein the insulating step comprises separating the expanding gas from the proximal and distal ends of the balloon with another balloon, the gas expanding step performed by inflating the other balloon into radial engagement against a central region of the surrounding balloon.

18. A method as claimed in claim 15, wherein the balloon inflating step is performed so as to leave cells lining the body lumen viable.

19. A method for treating hyperplasia of a blood vessel, the blood vessel having a target site along an inner surface, said method comprising:

introducing a catheter into the blood vessel;

positioning inner and outer nested balloons of the catheter proximate the target site within the blood vessel;

expanding the outer balloon with a fluid;

inflating the inner balloon by expanding a gas within the inner balloon so that the inner balloon radially engages the outer balloon and the outer balloon radially engages the inner surface of the blood vessel along the target site, wherein the expanding gas cools the inner surface of the body lumen to a temperature and for a time sufficient to inhibit subsequent excessive cell proliferation.

20. A method as claimed in claim 19, further comprising thermally insulating first and second ends of the outer balloon from the expanding gas with the fluid, the fluid separating the first and second ends of the outer balloon from first and second ends of the inner balloon during the inflating step.

* * * * *